US010774312B2

(12) United States Patent
Higa et al.

(10) Patent No.: US 10,774,312 B2
(45) Date of Patent: Sep. 15, 2020

(54) METHOD FOR PRODUCING FROZEN MESENCHYMAL CELLS AND METHOD FOR PRODUCING IMPLANTABLE THERAPEUTIC MEMBER

(71) Applicant: ADVANCED CELL TECHNOLOGY AND ENGINEERING LTD., Tokyo (JP)

(72) Inventors: Toshimitsu Higa, Tokyo (JP); Kenji Otani, Tokyo (JP); Koichi Otomo, Tokyo (JP)

(73) Assignee: ADVANCED CELL TECHNOLOGY AND ENGINEERING LTD., Tokyo (JP)

( * ) Notice: Subject to any disclaimer, the term of this patent is extended or adjusted under 35 U.S.C. 154(b) by 33 days.

(21) Appl. No.: 15/573,877

(22) PCT Filed: May 2, 2016

(86) PCT No.: PCT/JP2016/063589
§ 371 (c)(1),
(2) Date: Nov. 14, 2017

(87) PCT Pub. No.: WO2016/181885
PCT Pub. Date: Nov. 17, 2016

(65) Prior Publication Data
US 2018/0346880 A1 Dec. 6, 2018

(30) Foreign Application Priority Data

May 14, 2015 (JP) ................. 2015-098784

(51) Int. Cl.
| | | |
|---|---|---|
| C12N 5/0775 | (2010.01) | |
| A61K 35/28 | (2015.01) | |
| A61K 35/32 | (2015.01) | |
| A61L 27/00 | (2006.01) | |
| A61L 27/38 | (2006.01) | |
| A61L 27/54 | (2006.01) | |
| A61L 27/58 | (2006.01) | |
| C12N 5/077 | (2010.01) | |

(52) U.S. Cl.
CPC ............ *C12N 5/0664* (2013.01); *A61K 35/28* (2013.01); *A61K 35/32* (2013.01); *A61L 27/00* (2013.01); *A61L 27/3804* (2013.01); *A61L 27/3821* (2013.01); *A61L 27/3834* (2013.01); *A61L 27/54* (2013.01); *A61L 27/58* (2013.01); *C12N 5/0653* (2013.01); *C12N 5/0654* (2013.01); *A61L 2300/64* (2013.01); *A61L 2430/02* (2013.01); *A61L 2430/34* (2013.01); *C12N 2506/1361* (2013.01); *C12N 2509/00* (2013.01); *C12N 2523/00* (2013.01)

(58) Field of Classification Search
CPC .. C12N 5/0664; C12N 5/0654; C12N 5/0653; C12N 2509/00; C12N 2523/00; C12N 2506/1361; A61L 27/3834; A61L 27/54; A61L 27/58; A61L 27/3821; A61L 27/3804; A61L 2300/64; A61L 2430/02; A61L 2430/34; A61K 35/28
See application file for complete search history.

(56) References Cited

U.S. PATENT DOCUMENTS

| | | | | |
|---|---|---|---|---|
| 8,673,635 | B2 * | 3/2014 | Sokal ................. | C12N 5/0672 435/370 |
| 2013/0212724 | A1 * | 8/2013 | Yoshida ............... | A61K 35/36 800/18 |

FOREIGN PATENT DOCUMENTS

| | | |
|---|---|---|
| WO | 2008/133140 A1 | 11/2008 |
| WO | 2012/042618 A1 | 4/2012 |
| WO | 2013/146692 A1 | 10/2013 |
| WO | 2015/025810 A1 | 2/2015 |

OTHER PUBLICATIONS

Soleimani et al. A protocol for isolation and culture of mesenchymal stem cells from mouse bone marrow. Nature Protocols (2009), v4(1), p. 102-106. (Year: 2009).*
Garg et al. Non-enzymatic dissociation of human mesenchymal stromal cells improves chemokine-dependent migration and maintains immunosuppressive function. Cytotherapy (2014), 16, 545-559. (Year: 2014).*
Papaccio et al. Long-Term Cryopreservation of Dental Pulp Stem Cells (SBP-DPSCs) and Their Differentiated Osteoblasts: A Cell Source for Tissue Repair. Journal of Cellular Physiology (2006), 208, 319-325. (Year: 2006).*
Woods et al. Optimized cryopreservation method for human dental pulp-derived stem cells and their tissues of origin for banking and clinical use. Cryobiology (2009), 59, 150-157. (Year: 2009).*
Zhang et al. Multilineage Differentiation Potential of Stem Cells Derived from Human Dental Pulp after Cryopreservation. Tissue Engineering (2006), 12(10), 2813-2823. (Year: 2006).*
B. Perry et al: "Collection, Cryopreservation, and Characterization of Human Dental Pulp-Derived Mesenchymal Stem Cells for Banking and Clinical Use", Tissue Engineering, vol. 14, No. 2, pp. 149-156, 2008.

(Continued)

*Primary Examiner* — Sean C. Barron
(74) *Attorney, Agent, or Firm* — W&C IP

(57) ABSTRACT

It is an object of the present invention to provide a method for producing frozen mesenchymal cells maintaining a viability and an adhesion rate similar to those of cells obtained through a step of culture, without undergoing a step of culturing cells before cryopreservation step. The method comprises dissociating cells by treating a tissue with proteolytic enzymes and cryopreserving the cells. The present invention provides a method for producing frozen mesenchymal cells maintaining a viability and an adhesion rate similar to those of culturing cells without a step of culturings cells before cryopreserving.

7 Claims, 4 Drawing Sheets

(56) References Cited

OTHER PUBLICATIONS

"Revised Cultured Cell Experiment Handbook," 2008, Yodosha, pp. 77, 84.
"Is Your Way of Culturing Cells Okay?!," 2015, Yodosha, pp. 110-111.
Hideki Koyama, "Cell Culture Lab Manual," 1999, Springer-Verlag Tokyo pp. 52-54.
Kenmotsu et al., "Analysis of side population cells derived from dental pulp tissue", International Endodontic Journal, 2010, vol. 43, pp. 1132-1142.
Sigma Saibo Bayo Guide 2013 (Protocol-shu + Seihin Shokai), Aug. 2013, Web, accessed Aug. 5, 2016.

* cited by examiner

METHOD FOR PRODUCING FROZEN MESENCHYMAL CELLS AND METHOD FOR PRODUCING IMPLANTABLE THERAPEUTIC MEMBER

TECHNICAL FIELD

The present invention relates to a method for producing frozen mesenchymal cells and a method for producing an implantable therapeutic material.

BACKGROUND ART

Mesenchymal stem cells as one kind of somatic stem cells is a generic term for cells having the ability to differentiate into cells belonging to mesenchymal cells such as osteoblasts (bone cells), adipocytes (fat cells), myocytes (muscle cells) and chondrocytes (cartilage cells). Mesenchymal stem cells are considered to exist in all types of mesenchymal tissues, and are expected to be applied to regenerative medicine such as the reconstruction of bones, muscles, blood vessels, and nerves.

Cells may be contaminated with bacteria, fungus, and the like during a subculture and may undergo hereditary changes. Human diploid cells and primary cultured cells can proliferate only for a limited number of division cycles, and age through a subculture. For these reasons, cells that are not used for a certain period of time are preserved by freezing in an ultra-low temperature freezer or liquid nitrogen tank, and are thawed as needed.

For the same reasons, mesenchymal stem cells or a mesenchymal cell population including mesenchymal stem cells are preserved by freezing when they are not used for a certain period of time. When some subjects require the regeneration of bone, cartilage or skin tissue and medical treatment for myocardial infarction, cerebral infarction, spinal cord damage, and the like, mesenchymal stem cells or a mesenchymal cell population including mesenchymal stem cells matching the respective subjects or cell types are thawed, and implantable therapeutic materials are prepared. The thawed cells are then implanted into the subjects. It is expected that such implantation will produce therapeutic effects such as the regeneration of tissue.

It is known that cells in a logarithmic growth phase are best suited for cryopreservation. For example, Non-Patent Literatures 1 and 2 disclose that importance is placed on the state of cells before freezing, and cells in a logarithmic growth phase are suitable for cryopreservation. A typical example of cryopreservation methods for cells harvested from tissue is a method (Non-Patent Literature 3) including the following steps: (1) harvesting a tissue from an individual, (2) chopping up the harvested tissue and dissociating cells from the tissue by using a proteolytic enzyme such as trypsin or collagenase, (3) suspending the dissociated cells in a culture medium, (4) primarily culturing the cells under a proper environment, (5) subculturing the cells through the second and third passages, and (6) recovering the cells in a logarithmic growth phase to use the cells for cryopreservation. However, such a cell cryopreservation method needs to undergo a step of culturing cells before cryopreservation. This step is complicated. In addition, in a business requiring the cryopreservation of a large amount of cells, like a business using a cell bank, the cost required for reagents and devices for culturing cells and facilities such as a $CO_2$ incubator and space, etc., increases in proportion to the amount of cells to be cryopreserved. In addition, the time and labor needed for operations translate into high labor costs. Furthermore, such costs are reflected in end products and the like applied to final regenerative medicine. Under such circumstances, there have been demands for methods to reduce costs.

On the other hand, when tissue fragments harvested from an individual are directly frozen, the cells dissociated from the thawed tissue fragments exhibit a low viability and a low adhesion rate with respect to a culture flask and the like, resulting in difficulty in maintaining the cells as cultured cells.

CITATION LIST

Non-Patent Literature

Non-Patent Literature 1: "Revised Cultured Cell Experiment Handbook," 2008, YODOSHA, pp 77, 84
Non-Patent Literature 2: "Is Your Way of Culturing Cells Okay?!," 2015, YODOSHA, pp 110-111
Non-Patent Literature 3: Hideki Koyama, "Cell Culture Lab Manual," 1999, Springer-Verlag Tokyo pp 52-54

SUMMARY OF THE INVENTION

Problems to be Solved by the Invention

Under the circumstances, it is an object of the present invention to provide a method for producing frozen mesenchymal cells maintaining a high viability and a high adhesion rate by using a method simpler than conventional cryopreservation.

Means for Solving the Problem

First, the present inventors focused on culture periods for cells in order to simplify a step of culturing cells before a freezing treatment, and conducted studies on the shortening of culture periods. With the intention to restore cells dissociated from a tissue by an enzyme treatment from damage caused by cell ablation with an enzyme treatment, the inventors cultured the cells in a culture solution for two to three days and tried a freezing/thawing treatment with respect to the cells adhering on a culture dish. The result of the freezing/thawing treatment using the cells obtained by the above method, however, revealed that the viability of the cells after thawing and the adhesion rate of the cells with respect to a culture flask or the like were much lower than those in the conventional method for cryopreservation of cells in a logarithmic growth phase. In addition, this result matched the conventional finding that cells in a logarithmic growth phase were best suited for cryopreservation.

In consideration of such a result, the present inventors have made an amazing finding, upon making repeated earnest studies, that when mesenchymal cells dissociated from a tissue by a proteolytic enzyme treatment were cryopreserved without undergoing a culture step, the cells were able to maintain as high a viability and an adhesion rate as those of cells that were dissociated from a tissue by an enzyme treatment and were not cryopreserved. The present invention has been completed on the basis of the above finding.

That is, the present invention relates to

[1] a method for producing frozen mesenchymal cells, including:

a step of dissociating mesenchymal cells by treating a tissue containing mesenchymal cells with a mixture of two or more two types of proteolytic enzymes; and a step of cryopreserving the mesenchymal cells, the method not including a step of culturing mesenchymal cells before the step of cryopreserving the mesenchymal cells;

[2] the method for producing frozen mesenchymal cells according to [1], wherein the tissue containing the mesenchymal cells is a pulp tissue, and the mesenchymal cells comprise pulp cells;

[3] the method for producing frozen mesenchymal cells according to [1] or [2], wherein the mixture of the proteolytic enzymes comprises collagenase;

[4] the method for producing frozen mesenchymal cells according to [1] or [2], wherein the mixture of two or more two types of proteolytic enzymes is Accutase;

[5] the method for producing frozen mesenchymal cells according to any one of [1] to [4], further including a step of stopping an enzyme reaction after the step of dissociating the mesenchymal cells by the treatment with the mixture of the proteolytic enzymes;

[6] the method for producing frozen mesenchymal cells according to [5], wherein the step of stopping the enzyme reaction is performed by adding a serum;

[7] the method for producing frozen mesenchymal cells according to [5] or [6], further including a step of rinsing cells with which an enzyme reaction is stopped after the step of stopping the enzyme reaction;

[8] the method for producing frozen mesenchymal cells according to any one of [5] to [7], wherein the method does not comprise a step of filtering a cell suspension solution after the step of stopping the enzyme reaction;

[9] a method for producing an implantable therapeutic material, including a step of thawing frozen mesenchymal cells produced by a method for producing frozen mesenchymal cells according to any one of [1] to [8];

[10] the method for producing an implantable therapeutic material according to [9], further including a step of culturing thawed cells after the step of thawing frozen mesenchymal cells produced by the method for producing the frozen mesenchymal cells;

[11] the method for producing an implantable therapeutic material according to [10], further including a step of differentiating mesenchymal stem cells after the step of culturing the thawed cells; and

[12] a kit including frozen mesenchymal cells produced by a method for producing according to any one of [1] to [8] or an implantable therapeutic material produced by a method for producing an implantable therapeutic material according to any one of [9] to [11].

Effects of the Invention

According to the present invention, it is possible to produce frozen mesenchymal cells including cells dissociated from a tissue containing mesenchymal cells without undergoing a culture step, which is conventionally required, that is, "(4) primarily culturing the cells under a proper environment" or "(5) subculturing the cells through the second and third passages." This makes it possible to significantly reduce the time, cost, and labor required until cryopreservation. This, in turn, can produce a large amount of frozen mesenchymal cells at the same time, allowing a large amount of mesenchymal cells required in the future to be stocked. In addition, according to the present invention, it is possible to produce frozen mesenchymal cells including cells dissociated from a tissue containing mesenchymal cells while maintaining a high viability and an adhesion rate. Expected is the application of the present invention to regenerative medicine using mesenchymal stem cells comprised in the frozen mesenchymal cells.

BEST MODES FOR CARRYING OUT THE EMBODIMENTS

Figure 1:
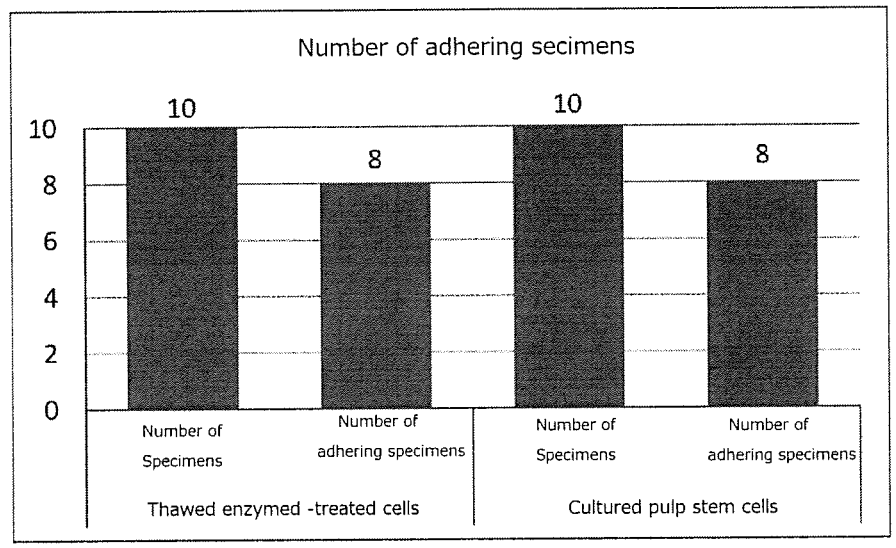
FIG. 1 is a graph showing the numbers of specimens concerning the adhesion of enzyme-treated cells and the adhesion of cultured pulp cells.

A method for producing frozen mesenchymal cells according to the present invention comprises a step of dissociating mesenchymal cells by treating a tissue containing the mesenchymal cells with a mixture of two or more types of proteolytic enzymes and a step of cryopreserving the obtained mesenchymal cells, and does not comprise a step of culturing the mesenchymal cells before the step of cryopreserving the mesenchymal cells.

In this specification, "mesenchymal cells" comprise mesenchymal stem cells. That is, the present invention allows for the replacement of "mesenchymal cells" with "mesenchymal stem cells" in an embodiment. For example, the present invention comprises the following embodiment;

A method for producing frozen mesenchymal cells, comprising a step of dissociating mesenchymal stem cells by treating a tissue containing the mesenchymal stem cells with a mixture of two or more types of proteolytic enzymes, and a step of cryopreserving the mesenchymal stem cells, wherein the method does not comprise a step of culturing the mesenchymal stem cells before the step of cryopreserving the mesenchymal stem cells.

In this specification, mesenchymal stem cells are mesenchymal-derived somatic stem cells, which have the ability to differentiate into cells belonging to the mesenchymal system.

In addition, in this specification, a tissue containing mesenchymal cells is a tissue containing mesenchymal-derived somatic stem cells. More specifically, although not limited to the following, such tissues comprise bone-marrow tissues, fat tissues, placental tissues, umbilical tissues, and pulp tissues.

A tissue containing mesenchymal cells can be isolated from a living body. Such a tissue may be harvested under the same conditions as those generally used for the harvesting of the tissue. The tissue may be extracted in an antiseptic condition and preserved in an appropriate preservation solution. More specifically, there are available a method for extracting a tissue from a living body with suction using a syringe, a method for harvesting a tissue by a surgical operation with local anesthesia of a living body, and the like.

In this specifically, proteolytic enzymes comprise collagenase, trypsin, hyaluronidase, elastase, pronase, and dispase, but are not limited to them. In addition, a mixture of two or more types of proteolytic enzymes is a mixture including two or more different types of proteolytic enzymes, and comprises, for example, a mixture of collagenase and pronase, a mixture of collagenase and trypsin, a mixture of collagenase and hyaluronidase, and a mixture of collagenase and dispase. Furthermore, a mixture of proteolytic enzymes is more preferably a mixture including no animal-derived components or microorganism-derived components. A mixture may comprise a buffer solution and other types of additives and the like suitable for so-called ready-to-use solutions.

A person skilled in the art can select a buffer solution used for a mixture including two or more types of proteolytic enzymes, as appropriate, and can use, for example, an acetic acid buffer, phosphoric acid buffer, citric acid buffer, boric acid buffer, tartaric acid buffer, tris buffer, or phosphate buffered saline. A suitable buffer solution can be selected in accordance with the types of proteolytic enzymes.

A mixture of two or more types of proteolytic enzymes may be a commercially available enzyme, for example, Accutase® available from Innovative Cell Technologies, Inc., Accumax® available from Innovative Cell Technologies, Inc., or the like.

In addition, when a combination of collagenase and dispase is used, it is possible to use, for example, a mixture of collagenase and dispase, which is obtained by mixing 5% dispase and 4% collagenase dissolved in PBS at a 1:1 ratio. Note that a person skilled in the art can adjust a concentration and a mixing ratio, as appropriate, for each proteolytic enzyme to be actually used.

Conditions such as the concentrations of enzymes used for a proteolytic enzyme treatment, a temperature, and a time can be determined as appropriate in accordance with the enzyme to be used. For example, an enzyme treatment may be performed under conditions that a temperature is in a range from 0° C. or higher to 37° C. or lower and that a time is in a range from 30 minutes or more to 6 hours or less. A proteolytic enzyme treatment may be performed two or more times. A person skilled in the art can select a treatment count as appropriate. Note that in a preferable embodiment, a step of a proteolytic enzyme treatment is performed only once. When, for example, a proteolytic enzyme treatment taking 30 minutes is to be performed twice, it is preferable to perform a proteolytic enzyme taking a total time corresponding to the method performing the treatment twice, that is, 1 hour, only once. Performing a proteolytic enzyme treatment only once is preferable because this can more gradually dissociate mesenchymal cells from a tissue. Performing a proteolytic enzyme treatment once is equivalent to performing once a step from placing a tissue and/or cells into a mixture including proteolytic enzymes to removing the mixture including the proteolytic enzymes from the tissue and/or the cells and/or adding a proteolysis inhibitor to the tissue and/or the cells.

When an enzyme treatment is to be performed only once with respect to, for example, human-derived pulp tissues, an enzyme treatment taking about 1 hour may be performed once at 37° C. In addition, even for a tissue derived from another animal, a person skilled in the art can set a temperature and a time suitable for an enzyme treatment to be performed once, as appropriate.

In this specification, "dissociating mesenchymal cells by treating a tissue containing the mesenchymal cells with a mixture of two or more types of proteolytic enzymes" comprises placing a tissue into a mixture including two or more types of proteolytic enzymes and ablating cells adhering to each other by reacting the enzymes, and isolating single cells from the tissue containing mesenchymal cells. A tissue may be pinched and chopped up with a scalpel, a pair of tweezers, and the like first, and then may be treated with enzymes. The entire tissue need not be chopped up into single cells. A person skilled in the art can adjust conditions for an enzyme treatment in accordance with cryopreservation.

In this specification, "cryopreserving cells" may be performed by a known method including, for example, a method can be performed by directly cryopreserving the storage container in which cell are suspended in a cell preservation solution, and a method can be performed cell freezing by transferring and preserving the storage container in a liquid nitrogen tank or deep freezer after freezing the container in a programmed freezer or Beissel freezing container.

In this specification, "preserving cells" indicates the preservation of cells in a state that allows the cells to be cultured after being frozen. Whether cells can be cultured can be determined by a known method. For example, this determination can be made by checking whether thawed cells disseminated in a culture flask are adhered to the culture flask or whether thawed cells can be subcultured.

Any type of cell preservation solution can be used as long as it can preserve the cells in a state that allows them to be cultured. For example, a serum may be used. It is possible to use a commercially available cell preservation solution such as CELLBANKER 1 (Nippon Zenyaku Kogyo Co., Ltd.), Culture Sure (Wako Pure Chemical Industries, Ltd.), or TC protector (DS Pharma Biomedical Co., Ltd.).

A cell preservation solution may contain a cryoprotective material. A cryoprotective material is a material to be added to a preservation solution to prevent various difficulties caused by cell freezing so as to maintain the function and viability of cells at the time of cryopreservation. For example, it is possible to use a sulfoxide such as dimethylsulfoxide (DMSO), ethylene glycol, glycerol, propanediol, propylene glycol, butanediol, or a chain polyol such as polyethylene glycol.

In this specification, "does not comprise a step of culturing the mesenchymal cells before the cryopreservation of the mesenchymal cells" means that the method does not comprise or does not substantially comprise a step of culturing the cells before the step of cryopreserving the cells after the step of dissociating the cells by treating the tissue with proteolytic enzymes. That "does not substantially comprise a step of culturing the cells" means that the method does not comprise a step of culturing the cells for a long period of time by using a culture solution or the like with the intention to cause the cells to adhere onto a culture dish and to proliferate or maintain the cells. Without such intention, placing cells in a culture solution for several minutes to several tens of minutes is not substantially comprised in a step of culturing cells. According to an embodiment, therefore, "a step of cryopreserving mesenchymal cells" comprises cryopreserving mesenchymal cells that are not adhering to a culture dish or free-floating mesenchymal cells. Note that a preferred embodiment does not completely comprise any step of placing cells in a culture solution before a step of cryopreserving the cells after a step of dissociating the cells by treating a tissue with proteolytic enzymes. The mesenchymal cells dissociated by an enzyme treatment are preferably immediately frozen.

In addition, in this specification, "culturing cells" indicates proliferating or maintaining cells in a container (flask or petri dish) containing a culture medium. A step of extracting a tissue from an individual, dissociating cells from the tissue, transferring the cells into a container containing a culture medium, and proliferating the cells until the first subculture is referred to as primary culture. A step of transferring existing cultured cells (including primarily cultured cells) to another container and proliferating the cells is referred to as subculture. Culture comprises primary culture and subculture.

Cells are cultured by leaving a container containing a culture medium to which cultured cells adhere to stand in an incubator under conditions of a temperature of 37° C., a humidity of 100%, and a $CO_2$ concentration of 5%. A person skilled in the art can determine, as appropriate, conditions such as a temperature, humidity, and $CO_2$ concentration in accordance with the type of cells.

A culture medium to be used is not specifically limited. For example, it is possible to use commercially available culture media used for a cell culture, such as Eagle's minimal essential culture medium (MEM culture medium), Dulbecco's modified Eagle's culture medium (DEMM culture medium), Iscove's modified Dulbecco's culture medium (IMDM culture medium), RPMI-1640 culture medium, $\alpha$-MEM culture medium, F'-12 culture medium, and AIM-V culture medium. The following serums can be added to culture media as needed: fetal bovine serum (FBS, FCS), newborn calf serum (NBS), calf serum (CS), adult cattle serum, horse serum, pig serum, rabbit serum, goat serum, and human serum. In addition, various types of additives may be added to culture media, as needed.

The method for producing frozen mesenchymal cells according to the present invention comprises a step of dissociating pulp cells by treating a pulp tissue with a mixture of two types of proteolytic enzymes, and a step of cryopreserving the obtained pulp cells, and does not comprise a step of culturing the pulp cells before the step of cryopreservation of the pulp cells.

Pulp tissues in this specification can be harvested from both a primary tooth and a permanent tooth, and can also be obtained from the pulp of an extracted tooth such as a primary tooth or third molar tooth which has been treated as medical waste. A pulp tissue can be extracted from a tooth extracted by a dental procedure in a dental clinic or a tooth extracted naturally. For example, a tooth extracted by a dental procedure, which cannot be frozen on-site, can be preserved at a low temperature (for example, 4° C.) while being immersed in a culture medium such as $\alpha$-MEM for transportation.

In addition, a mammal from which a pulp tissue is derived is not limited to a human, and may be another mammal (for example, a mouse, rat, rabbit, dog, cat, monkey, sheep, cow, or horse).

Pulp cells can be obtained from a pulp tissue. In addition, pulp cells derived from a pulp tissue comprise pulp stem cells. A pulp stem cell is a type of tissue stem cell which can be isolated from the pulp. A tissue stem cell is also referred to as a somatic stem cell, which can be differentiated into only limited types of cells, in contrast to an embryonic stem cell that can be differentiated into all types of cells.

The method for producing frozen mesenchymal cells according to the present invention may further comprise a step of stopping an enzyme reaction after a step of dissociating mesenchymal cells by a treatment with a mixture of proteolytic enzymes.

An enzyme reaction can be stopped by adding a proteolysis inhibitor. As a proteolysis inhibitor, an inhibitor for a proteolytic enzyme used in a step of a proteolytic enzyme treatment can be used. When, for example, an enzyme used in a step of a proteolytic enzyme treatment is trypsin, a trypsin inhibitor can be used. In addition, a serum comprises various types of proteolysis inhibitors, and hence can be used as a proteolysis inhibitor. An enzyme reaction may be stopped by adding a proteolysis inhibitor or serum to a culture medium and adding the culture medium to a mixture of proteolytic enzymes in which a tissue has been dissociated.

Note that depending on a proteolytic enzyme to be used, no proteolysis inhibitor needs to be added to stop an enzyme reaction. In such a case, it suffices if an enzyme is diluted to lose its activity by adding a culture medium containing no component serving as an inhibitor to the enzyme (animal-derived serum or soybean-derived proteolysis inhibitor), PBS, serum-free culture medium, or the like to the culture medium. Alternatively, such an enzyme solution may be directly replaced with a cryopreservation solution or another culture medium, or a rinsing step to be described below may be directly performed. That is, the step of stopping an enzyme reaction can be performed by diluting the enzyme with a culture medium including no component serving as an enzyme inhibitor, PBS, or serum-free culture medium.

The method for producing frozen mesenchymal cells according to the present invention may further comprise a step of rinsing cells in a solution which an enzyme reaction has been stopped after the step of stopping the enzyme reaction. Cells are rinsed by, for example, adding a sufficient amount of buffer solution such as a phosphoric acid buffer solution to the cells, rinsing the cells, and discarding the phosphoric acid buffer solution and the like. The step of adding a phosphoric acid buffer solution to cells rinsed once, rinsing the cells, and discarding the phosphoric acid buffer solution and the like may be repeated several times. A person skilled in the art can select, as appropriate, the amount of buffer solution and the number of times of rinsing.

In addition, according to an embodiment, the method for producing frozen mesenchymal cells according to the present invention does not comprise a step of filtering a cell suspension solution after a step of stopping an enzyme reaction. Note that "filtering a cell suspension solution" indicates filtering a cell suspension solution containing mesenchymal cells obtained by an enzyme treatment or in a rinsing step after an enzyme treatment by using a nylon mesh or cell strainer. It is preferable in terms of reducing damage to cells to omit such a filtering step.

A method for producing an implantable therapeutic material according to the present invention comprises a step of thawing frozen mesenchymal cells produced by the above method for producing frozen mesenchymal cells.

In this specification, "thawing cells" indicates thawing cells, which can be performed in accordance with a method known by the person skill in the art. For example, cells may be thawed by removing a storage container in which cells are suspended from a nitrogen tank or deep freezer and immersing the container in a warm bath at 37° C. to thaw the cells as quickly as possible.

The method for producing an implantable therapeutic material according to the present invention may further comprise a step of culturing thawed cells after a step of thawing frozen mesenchymal cells produced by the method for producing frozen mesenchymal cells described above.

A person skilled in the art can perform the step of "culturing thawed cells" in accordance with a known method. For example, a person skilled in the art may perform this step by (1) suspending rapidly thawed cells in a culture medium, (2) performing centrifugal separation of the cell suspension solution and removing the supernatant, (3) adding a culture medium to precipitated cells, and (4) disseminating cells to a T-75 flask and proliferating the cells in an incubator at a temperature of 37° C., a humidity of 100%, and a $CO_2$ concentration of 5%.

The method for producing an implantable therapeutic material according to the present invention may comprise a step of differentiating mesenchymal stem cells obtained by culturing after a step of culturing thawed cells.

In this specification, "differentiating mesenchymal stem cells" indicates exposing the mesenchymal stem cells to an inducer to differentiate the cells into osteoblasts (bone cells), adipocytes (fat cells), chondrocytes (cartilage cells), neurocytes (nerve cells), cardiomyocytes (myocardial cells), hepatocytes (hepatic cells), vascular cells, and the like. Such a differentiation induction method is known. Induction materials known to be used for differentiation into bone cells comprise 10% serum, dexamethasone, β-glycerophosphoric acid, and ascorbic acid, and those known to be used for differentiation into fat cells comprise dexamethasone, 1-methyl-3-isobutylxanthine, insulin, indomethacin and the like. Adding such an induction material to a culture medium will lead to differentiation induction. It is possible to use commercially available culture medium additives containing induction materials for differentiating mesenchymal stem cells into various types of cells. Commercially available materials such as counterstains can be used to evaluate and determine whether differentiation into various types of cells has occurred.

An implantable therapeutic material produced by the method for producing an implantable therapeutic material according to the present invention can be implanted into a region expected to be regenerated, such as a bone, muscle, blood vessel, or nerve, by means of drip fusion, a catheter, or the like. Alternatively, such a region may be treated by incising the region and implanting an implantable therapeutic material thereinto. It is possible to use another type of medicine together with this implantation as long as a therapeutic effect can be obtained. A person skilled in the art can determine, as appropriate, the amount and number of times of implantation of a therapeutic material.

A treatment subject is not limited to a human, and may be another mammal (for example, a mouse, rat, rabbit, dog, cat, monkey, sheep, cow, or horse).

In an implantable therapeutic material produced by the method for producing an implantable therapeutic material according to the present invention, mesenchymal stem cells derived from an implantation subject or mesenchymal stem cells derived from a person other than the implantation subject may be used. When mesenchymal stem cells derived from a person other than the implantation subject are to be used, for example, cells matching in human leukocyte antigen (HLA) may be selected from a cell bank and used.

An embodiment of the present invention comprises a kit including frozen mesenchymal cells produced by the above production method or the above implantable therapeutic material. This kit may comprise a culture medium for culturing a mesenchymal cell population including mesenchymal stem cells or all or some of the components of the culture medium. In addition to a culture medium, the kit may comprise a differentiation inducer, a reagent for evaluating differentiation, the coating material of a culture medium container, various types of reagents, a buffer solution, and a user manual.

The present invention will be described in more detail below with reference to Examples. However, the present invention is not limited to them.

EXAMPLES

Preparation of Reagents (1) 200 mM L-Ascorbic Acid Solution

L-ascorbic acid (Wako Pure Chemical Industries, Ltd.) of 1.76 g was dissolved in 50 mL of Otsuka distilled water.

(2) α-MEM Solution

α-MEM (GIBCO) of 39.5 mL, 10 mL of FBS (NICHIREI CORPORATION), 500 μL, of P/S (GIBCO), and 25 μL, of a 200 mM L-ascorbic acid solution were mixed together.

(3) Rinse PBS

PBS(−) (GIBCO) of 49 mL, 1 mL of FBS (NICHIREI CORPORATION), and 500 μL of P/S (GIBCO) were mixed with each other.

(4) Cell Preservation Solution

Cryosery (DMSO) (NIPRO) of 100 μL, and 900 μL of FBS (NICHIREI CORPORATION) were mixed with each other.

Example 1

Cryopreservation of Cells Treated with Enzyme and Culture of Thawed Cells (1) Extraction of Pulp Tissue After a tooth was dentally extracted, a pulp tissue was placed in a 15 mL sterile tube filled with an α-MEM solution so as to be immersed in the α-MEM solution. The pulp tissue was then refrigerated at a low temperature (4° C.) and preserved for 24 hours including the transportation time.

The tooth was removed into a sterile petri dish, and a pulp tissue was extracted by using a pair of tweezers and a reamer. The pulp tissue was transferred into a test tube and rinsed with 3 mL of rinse PBS. The pulp tissue was naturally precipitated, and the supernatant was discarded. The precipitated pulp tissue was further rinsed with 3 mL of rinse PBS. This rinsing process was further repeated three times. That is, rinsing was performed five times in total.

(2) Proteolytic Enzyme Treatment

After the fifth rinsing process in (1), the supernatant was discarded, and 6 mL of 37° C. Accutase was added to the precipitated pulp tissue, and an enzyme treatment was performed on the pulp tissue for 1 hour. Meanwhile, pipetting was repeated once per 10 minutes to dissociate pulp cells. Pipetting was performed 20 times. After a 1-hour enzyme treatment, 9 mL of α-MEM solution ice-cooled to 4° C. was added into the tube to stop the enzyme reaction. Centrifugal separation was performed at 100×g and room temperature for 5 minutes to precipitate pulp cells. The supernatant α-MEM solution was discarded. An α-MEM solution of 3 mL was added to the above solution again. A half amount of the resultant solution was used for the test in Reference Example 1 described below. The other half amount of the solution was subjected to centrifugal separation at 100×g and room temperature for 5 minutes to precipitate pulp cells. The supernatant α-MEM solution was discarded. Rinse PBS of 3 mL was added to the solution. The resultant solution was subjected to centrifugal separation at 100×g and room temperature for 5 minutes to precipitate pulp cells. The supernatant α-MEM solution was discarded.

(3) Cryopreservation

A 4° C. cell preservation solution of 1 mL was added to the pulp cells obtained in (2). The entire resultant solution was transferred into a Cryo Tube. The Cryo Tube was frozen overnight in a −80° C. freezer. The Cryo Tube was then transferred into a −150° C. freezer and preserved.

(4) Culture of Thawed Pulp Cells

The cryopreserved pulp cells (to be referred to as "enzyme-treated cells" hereinafter) obtained in (3) were thawed until the cell preservation solution was thawed in a 37° C. water bath and peeled off the side surface of the Cryo Tube. The thawed contents of the Cryo Tube were transferred into a 15 mL tube filled with 6 mL of an α-MEM solution heated to 37° C. The Cryo Tube was rinsed with 2 mL of an α-MEM solution (1 mL×2 times). The solution was then subjected to centrifugal separation at 100×g and room temperature for 5 minutes. The supernatant was discarded. An α-MEM solution of 500 μL was added to the precipitated pulp cells. This α-MEM solution of 20 μL and 20 μL of Trypan Blue were mixed with each other, and the numbers of cells were measured as "disseminated cell counts" by a counting chamber. After the cell count measurement, 4.5 mL of an α-MEM solution was added to the above solution to obtain 5 mL of the solution in total. Cells were then disseminated and cultured in a T-25 flask.

The adhesion of cells to a flask was confirmed in eight cases out of 10 cases (Table 1).

In Table 1, "freezing period" indicates the number of days until thawing of the cells after transfer into the −80° C. freezer. In addition, "adhesion confirmation date" indicates the date when it was confirmed that one to two cells of disseminated cells adhered to a flask on a given date (the date before the adhesion confirmation date), and formed a colony on the following date.

The rinse PBS of 2 mL was added into the tube again. Tapping was then performed, and the supernatant rinse PBS was discarded.

Subsequently, 3 mL of 37° C. Accutase was added to the precipitated pulp tissue, and an enzyme treatment was performed for 1 hour. Meanwhile, pipetting was repeated 20 times per 20 minutes to dissociate pulp cells. After a 1-hour enzyme treatment, the resultant solution was entirely transferred into a 15 mL tube filled with 10 mL of ice-cooled α-MEM solution, and the enzyme reaction was stopped. Centrifugal separation was performed at 100×g and room temperature for 5 minutes to precipitate pulp cells. The supernatant α-MEM solution was discarded.

(4) Culture of Pulp Cells

The pulp cells obtained in (3) were filtered through a nylon mesh (pore size: 70 μm) to recover single cells. The recovered cells were transferred into a 15 mL tube and subjected to centrifugal separation at 100×g and room temperature for 5 minutes to precipitate the pulp cells. The supernatant was discarded. An α-MEM solution of 2.5 mL was added to the recovered pulp cells. The cells were then disseminated and cultured in a T-12.5 flask.

The adhesion of cells to the flask was not able to be confirmed in all 10 cases.

TABLE 1

Adhesion of Thawed Enzyme-Treated Cells

|   | ID | Age | Sex | Number of Disseminated Cells ($1 * 10^4$) | Culture Start Date | Adhesion Confirmation Date | Freezing Period |
|---|---|---|---|---|---|---|---|
| 1 | YDP-15 | 9 | Female | 0.75 | Nov. 5, 2014 | Nov. 10, 2014 | 21 |
| 2 | YDP-16 | 9 | Female | 1.75 | Nov. 5, 2014 | Nov. 10, 2014 | 20 |
| 3 | YDP-17 | 9 | Female | 0.5 | Nov. 10, 2014 | No adhesion | 25 |
| 4 | YDP-18 | 12 | Male | 0.5 | Nov. 10, 2014 | Nov. 13, 2014 | 24 |
| 5 | YDP-19 | 10 | Male | 22.5 | Nov. 10, 2014 | Nov. 12, 2014 | 23 |
| 6 | YDP-20 | 10 | Female | 0.25 | Nov. 11, 2014 | Nov. 15, 2014 | 22 |
| 7 | YDP-21 | 10 | Female | 0.75 | Nov. 11, 2014 | Nov. 14, 2014 | 22 |
| 8 | YDP-22 | 10 | Male | 0 | Nov. 11, 2014 | No adhesion | 22 |
| 9 | YDP-23 | 8 | Male | 1.5 | Nov. 12, 2014 | Nov. 15, 2014 | 20 |
| 10 | YDP-24 | 13 | Female | 0.75 | Nov. 12, 2014 | Nov. 17, 2014 | 16 |

Comparative Example 1. Cryopreservation of Pulp Tissue without Enzyme-Treatment and Cell Culture after Thawing (1) Extraction of Pulp Tissue A pulp tissue was extracted by the same method as that in (1) of Example 1, and was rinsed five times with rinse PBS.

(2) Cryopreservation

After rinsing in (1), 1 mL of cooled cell preservation solution was added to the naturally precipitated pulp tissue, and the total amount of resultant solution was transferred into the Cryo Tube. The Cryo Tube was frozen overnight in a −80° C. freezer and then preserved.

(3) Proteolytic Enzyme Treatment

The cryopreserved pulp tissue obtained in (2) was thawed in a 37° C. water bath. The pulp tissue was transferred into a 15 mL tube filled with 10 mL of rinse PBS by using a pair of tweezers. Thereafter, the tissue was naturally precipitated, and the supernatant rinse PBS was discarded, and 2 mL of rinse PBS was added into the tube again. Tapping was then performed, and the supernatant rinse PBS was discarded.

Reference Example 1. Culture of Pulp Cells (without Cryopreservation)

(1) Extraction of Pulp Tissue

Reference Example 1 used one (half amount) of two pulp cell populations obtained by halving the pulp cell population prepared in (1) and (2) of Example 1.

(2) Culture of Pulp Cells

An α-MEM solution of 3.5 mL was added to the pulp cells (to be referred to as "cultured pulp cells" hereinafter) obtained in (1) and (2) of Example 1 to obtain 5 mL of solution in total. The cells were then disseminated in a T-25 flask, and culture was started.

The adhesion of cells to a dish was confirmed in eight specimens out of 10 specimens (Table 2).

The number of disseminated cells was obtained by measuring, with a counting chamber, the number of cells obtained by adding 500 μL of an α-MEM solution to the pulp cells obtained by centrifugal separation in (2) (4.5 mL of an α-MEM solution was added to the solution after measurement of the number of cells to obtain 5 mL of solution in total), and mixing 20 μL of the α-MEM solution with 20 μL of Trypan Blue.

TABLE 2

Cell Adhesion of Cultured Pulp Cells

| | ID | Age | Sex | Number of Disseminated Cells (1 * 10$^4$) | Culture Start Date | Adhesion Confirmation Date |
|---|---|---|---|---|---|---|
| 1 | YDP-15 | 9 | Female | 2 | Oct. 15, 2014 | Oct. 21, 2014 |
| 2 | YDP-16 | 9 | Female | 33 | Oct. 16, 2014 | Oct. 18, 2014 |
| 3 | YDP-17 | 9 | Female | 2.25 | Oct. 16, 2014 | No adhesion |
| 4 | YDP-18 | 12 | Male | 33 | Oct. 17, 2014 | Oct. 21, 2014 |
| 5 | YDP-19 | 10 | Male | 38.5 | Oct. 18, 2014 | Oct. 21, 2014 |
| 6 | YDP-20 | 10 | Female | 3.375 | Oct. 20, 2014 | Oct. 25, 2014 |
| 7 | YDP-21 | 10 | Female | 5.375 | Oct. 20, 2014 | Oct. 25, 2014 |
| 8 | YDP-22 | 10 | Male | 0 | Oct. 20, 2014 | No adhesion |
| 9 | YDP-23 | 8 | Male | 33.85 | Oct. 23, 2014 | Oct. 27, 2014 |
| 10 | YDP-24 | 13 | Female | 0.875 | Oct. 27, 2014 | Oct. 31, 2014 |

Test Example 1. Adhesion of Thawed Enzyme-Treated Cells (Example 1) and Cultured Pulp Cells (Reference Example 1)

Thawed enzyme-treated cells (Example 1) were compared in the number of adhering specimens and average number of days taken for adhesion with cultured pulp cells (Reference Example 1).

Figure 2:
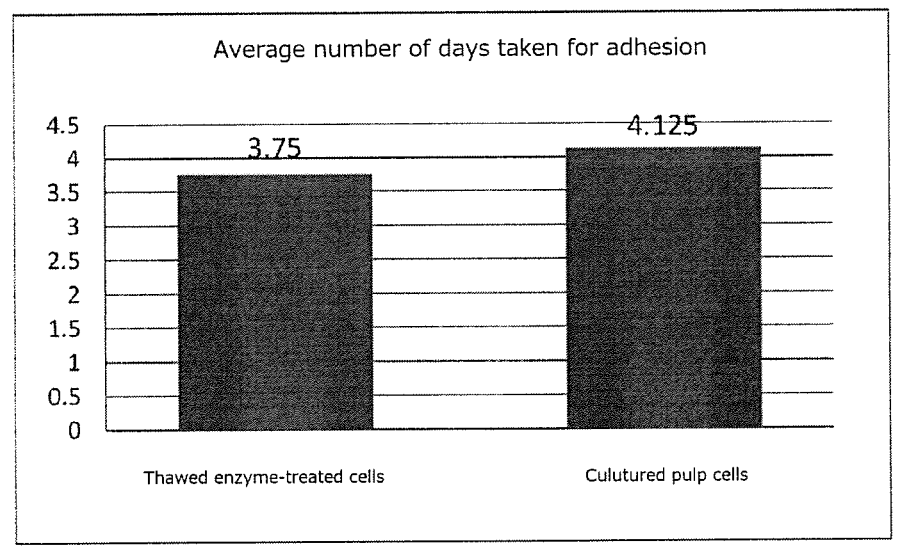
FIG. 2 is a graph showing the average numbers of days taken for the adhesion of enzyme-treated cells and the adhesion of cultured pulp cells.

The adhesion of cells in either case was confirmed in eight specimens out of 10 specimens (Table 3, FIG. 1). No difference was recognized in the average number of days taken for adhesion between the two cases (Table 3, FIG. 2). It was confirmed that the method according to the present invention can obtain a viability similar to that of cells cultured without a cryopreserving process, even by culturing through a cryopreserving process.

TABLE 3

Adhesion of Thawed Enzyme-Treated Cells and Number of Days Taken for Adhesion by Cultured Pulp Stem Cells

| | | Thawed Enzyme-Treated Cells | | Cultured Pulp Stem Cells | |
|---|---|---|---|---|---|
| | ID | Adhesion/ No Adhesion | Number of Days until Adhesion | Adhesion/ No Adhesion | Number of Days until Adhesion |
| 1 | YDP-15 | Adhesion | 5 | Adhesion | 6 |
| 2 | YDP-16 | Adhesion | 5 | Adhesion | 2 |
| 3 | YDP-17 | No adhesion | | No adhesion | |
| 4 | YDP-18 | Adhesion | 3 | Adhesion | 4 |
| 5 | YDP-19 | Adhesion | 2 | Adhesion | 3 |
| 6 | YDP-20 | Adhesion | 4 | Adhesion | 5 |
| 7 | YDP-21 | Adhesion | 3 | Adhesion | 5 |
| 8 | YDP-22 | No adhesion | | No adhesion | |
| 9 | YDP-23 | Adhesion | 3 | Adhesion | 4 |
| 10 | YDP-24 | Adhesion | 5 | Adhesion | 4 |

Test Example 2. Average Numbers of Days until Subculture of Thawed Enzyme-Treated Cells (Example 1) and Cultured Pulp Cells (Reference Example 1)

The average numbers of days until the cells in T-25 flasks were 80% to 90% confluent in the two cases were compared with each other.

Figure 3:
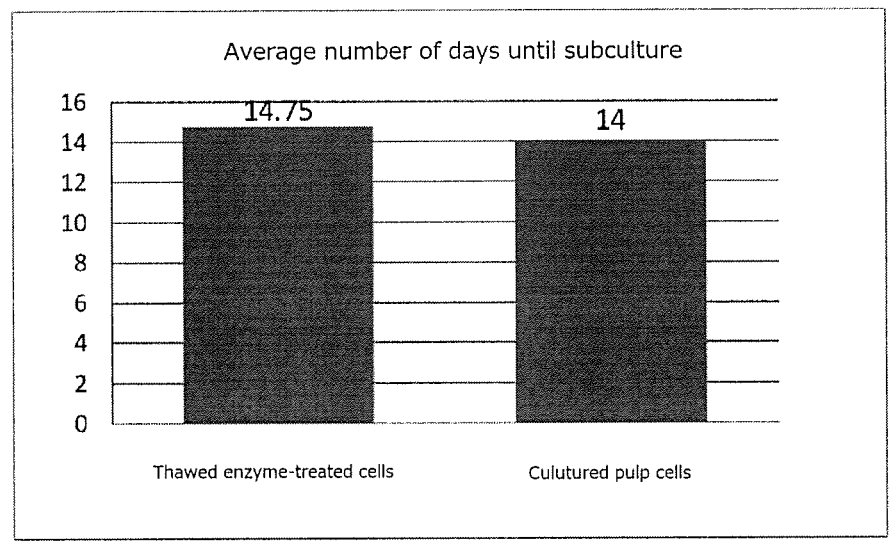
FIG. 3 is a graph showing the average numbers of days taken until the subculture of enzyme-treated cells and cultured pulp cells.

No difference was recognized in the number of days until subculture of cells between the two cases. This revealed that there was no difference in cell proliferation rate (Table 4, FIG. 3).

TABLE 4

Numbers of Days Until Subculture of Thawed Enzyme-Treated Cells and Cultured Pulp Cells

| | ID | Thawed Enzyme-Treated Cells | Cultured Pulp Stem Cells |
|---|---|---|---|
| 1 | YDP-15 | 20 | 16 |
| 2 | YDP-16 | 15 | 11 |
| 3 | YDP-17 | | |
| 4 | YDP-18 | 15 | 10 |
| 5 | YDP-19 | 11 | 10 |
| 6 | YDP-20 | 15 | 15 |
| 7 | YDP-21 | 14 | 15 |
| 8 | YDP-22 | | |
| 9 | YDP-23 | 13 | 20 |
| 10 | YDP-24 | 15 | 15 |
| | Average Number of days | 14.75 | 14 |

Test Example 3. Morphological Comparison between Thawed Enzyme-Treated Cells (Example 1) and Cultured Pulp Cells (Reference Example 1)

Figure 4:
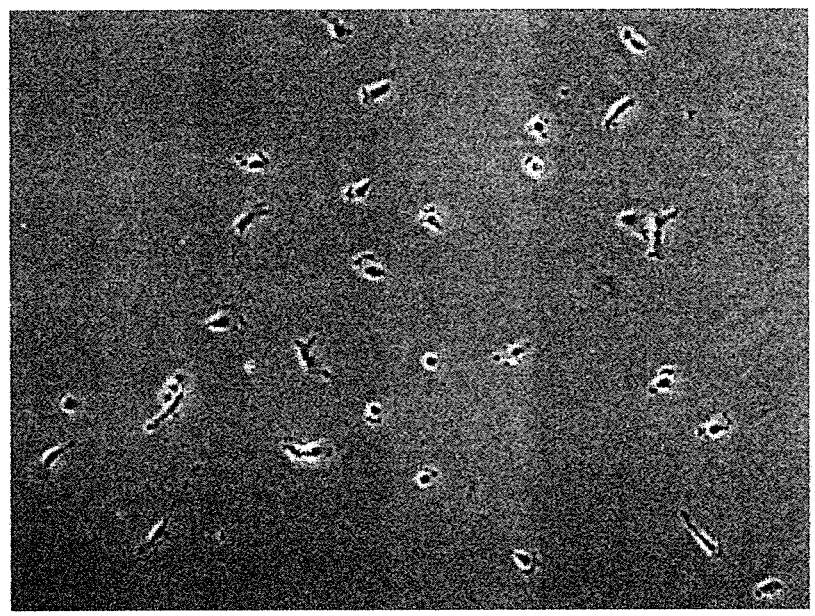
FIG. 4 is a view showing the form of enzyme-treated cells.
Figure 5:
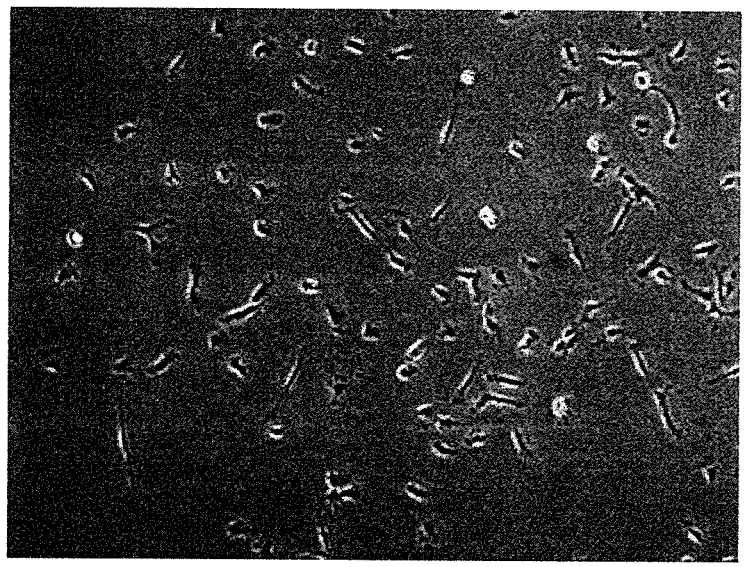
FIG. 5 is a view showing the form of cultured pulp cells.

A morphological comparison was made between enzyme-treated cells during a culture (FIG. 4) and cultured pulp cells (FIG. 5) with an inverted phase contrast microscope.

No morphological difference was recognized between the cells in the two cases.

Test Example 4. CFU-F Assay and Differentiation Induction of Thawed Enzyme-Treated Cells (Example 1)

CFU-F assay and differentiation induction were performed with respect to a colony formed by the thawed enzyme-treated cells obtained in Example 1 to check whether pulp stem cells were comprised.

After the adhesion of the thawed enzyme-treated cells obtained in Example 1 to a flask was confirmed, the cells were further cultured for 1 week by using an α-MEM solution to make the cells form a colony. CFU-F assay and differentiation induction were performed with respect to the colony. In addition, CFU-F assay and a differentiation induction method were performed to conduct tests and evaluation in accordance with the method described in a known literature (Sato et al., "Characterization of mesenchymal progenitor cells in crown and root pulp from human mesiodentes," Oral Dis. 2015 January; 21 (1):e86-89). The result confirmed that the thawed enzyme-treated cells obtained in Example 1 form a CFU-F colony and have the ability to differentiate into osteoblasts (bone cells) and adipocytes (fat cells).

The invention claimed is:

1. A method for producing frozen mesenchymal cells, comprising:
   dissociating mesenchymal cells by treating a tissue containing mesenchymal cells with a mixture of two or more types of proteolytic enzymes, wherein the tissue containing the mesenchymal cells is a pulp tissue, and the mesenchymal cells comprise pulp cells; and
   without culturing the mesenchymal cells, cryopreserving the mesenchymal cells.

2. The method for producing frozen mesenchymal cells according to claim 1, wherein the mixture of two or more types of proteolytic enzymes comprises collagenase.

3. The method for producing frozen mesenchymal cells according to claim 1, wherein the mixture of two or more types of proteolytic enzymes comprises trypsin and collagenase.

4. The method for producing frozen mesenchymal cells according to claim 1, further comprising a step of stopping an enzyme reaction after the step of dissociating the mesenchymal cells by the treatment with the mixture of two or more types of proteolytic enzymes.

5. The method for producing frozen mesenchymal cells according to claim 4, wherein the step of stopping the enzyme reaction is performed by adding a serum.

6. The method for producing frozen mesenchymal cells according to claim 4, further comprising a step of rinsing cells after the step of stopping the enzyme reaction.

7. The method for producing frozen mesenchymal cells according to claim 4, wherein the method does not comprise a step of filtering a cell suspension solution after the step of stopping the enzyme reaction.

* * * * *